United States Patent [19]
Sheridan et al.

[11] Patent Number: 5,780,227
[45] Date of Patent: Jul. 14, 1998

[54] OLIGONUCLEOTIDE PROBE CONJUGATED TO A PURIFIED HYDROPHILIC ALKALINE PHOSPHATASE AND USES THEREOF

[76] Inventors: Patrick J. Sheridan, 2008 Horne St., San Leandro, Calif. 94578; Julio C. Gagne, Studio #7, 5865 Doyle St., Emeryville, Calif. 94608; Mary L. Anderson, 1392 Danville Blvd #202, ALamo, Calif. 94507

[21] Appl. No.: 472,756

[22] Filed: Jun. 7, 1995

[51] Int. Cl.$^6$ .............................. C12Q 1/68; C07H 21/04; C07H 21/02
[52] U.S. Cl. .......................... 435/6; 536/23.1; 536/24.3; 935/77; 935/78
[58] Field of Search ................. 435/6; 536/23.1, 536/24.3; 935/77, 78

[56] References Cited

U.S. PATENT DOCUMENTS

| | | |
|---|---|---|
| 4,868,105 | 9/1989 | Urdea et al. |
| 4,894,325 | 1/1990 | Englehardt et al. |
| 5,124,246 | 6/1992 | Urdea et al. |
| 5,254,469 | 10/1993 | Warren, III et al. |

FOREIGN PATENT DOCUMENTS

| | | |
|---|---|---|
| 0254051 | 1/1988 | European Pat. Off. |
| 0 317 077 A1 | 5/1989 | European Pat. Off. |
| 0 417 841 A2 | 3/1991 | European Pat. Off. |
| 0 417 841 A3 | 3/1991 | European Pat. Off. |
| WO 93/13221 | 7/1993 | WIPO |
| WO 93/13223 | 7/1993 | WIPO |
| WO 93/13227 | 7/1993 | WIPO |

OTHER PUBLICATIONS

Jablonski et al. Nucl;eic Acids Research 14 (15) : 6115–6128 (1986).

Bublitz et al., "Heterogeneity of glycosylphosphatidylinositol–anchored alkaline phosphatase of calf intestine" *Eur. J. Biochem.* 217:199–207 (1993).

Schaap et al., "Chemical and enzymatic triggering of 1, 2–dioxetanes. 3: Alkaline phosphatase–catalyzed chemiluminescence from an aryl phosphate–substituted dioxetane" *Tet. Lett.* 27:1159–1162 (1987).

Enrico Davini et al., "Alkaline Phosphatase Inhibitors as Labels of DNA Probes." Elsevier Science Pub. Co., Inc. *GATA* 9(2):39–47, (1992).

Renz et al., Nucleic Acids Research 12(8): 3435–3444 (1984).

*Primary Examiner*—Stephanie W. Zitomer
*Assistant Examiner*—Ethan Whisenant
*Attorney, Agent, or Firm*—Kenneth Barovsky; Kenneth M. Goldman; Robert P. Blackburn

[57] ABSTRACT

A method of preparing a homogeneous alkaline phosphatase-oligonucleotide probe conjugate having high specific enzyme activity for use in nucleic acid hybridization assays is disclosed. Indirect, competitive nucleic acid hybridization assay formats are also described.

23 Claims, 2 Drawing Sheets

5,780,227

OLIGONUCLEOTIDE PROBE CONJUGATED TO A PURIFIED HYDROPHILIC ALKALINE PHOSPHATASE AND USES THEREOF

TECHNICAL FIELD

This invention relates generally to nucleic acid chemistry and hybridization assays. More particularly, the invention relates to methods for preparing labeled oligonucleotides which provide a signal with high specific activity of detection and which generates a target-dependent signal in nucleic acid hybridization assays by minimizing background noise deriving primarily from the use of a heterogeneous population of labeled probes. The invention also has applications in genotyping, antisense and aptamer therapeutics, mutational analysis and discontinuous probe mapping.

BACKGROUND

Nucleic acid hybridization assays are commonly used in genetic research, biomedical research and clinical diagnostics. In a basic nucleic acid hybridization assay, single-stranded analyte nucleic acid is hybridized to a labeled single-stranded nucleic acid probe and resulting labeled duplexes are detected. Variations of this basic scheme have been developed to enhance accuracy, facilitate the separation of the duplexes to be detected from extraneous materials, and/or amplify the signal that is detected.

One such assay is described in detail in commonly assigned U.S. Pat. No. 4,868,105 to Urdea et al., the disclosure of which is incorporated herein by reference. That assay involves the use of a two-part capturing system designed to bind the polynucleotide analyte to a solid support, and a two-part labeling system designed to bind a detectable label to the polynucleotide analyte to be detected or quantitated. The two-part capture system involves the use of capture probes bound to a solid support and capture extender molecules that hybridize both to a segment of the capture probes and to a segment of the polynucleotide analyte. The two-part labeling system involves the use of label extender molecules that hybridize to a segment of the polynucleotide analyte, and labeled probes that hybridize to the label extender molecules and contain or bind to a detectable label.

Alkaline phosphatase-oligonucleotide conjugates (see, e.g., EP 883096976) are often used as the signal-generating component of such hybridization assays. Adding an appropriate substrate, e.g., an enzyme-triggered dioxetane phosphate (Schaap et al., *Tet. Lett.* 28:1159–1162 (1987) and EPA Pub. No. 0254051) yields a detectable chemiluminescent signal. However, the background noise level may not be ideal in such assays due, in part, to the heterogeneous population of alkaline phosphatase molecules available for conjugation, which contributes to nonspecific binding of labeled probes. Low signal-to-noise ratios may also result from the preparation of alkaline phosphatase-labeled probes by conjugation of oligonucleotides to the enzyme under conditions that permit conjugation to reactive sites in or near the active site of the enzyme, thereby reducing the alkaline phosphatase specific enzyme activity.

Alkaline phosphatase is typically obtained from bovine or calf intestinal mucosa. Highly purified alkaline phosphatase can be obtained in a four-step process that yields hydrophilic and hydrophobic fractions of the enzyme (Bublitz et al. (1993) *Eur. J. Biochem.* 217:199–207).

Bovine or calf intestinal alkaline phosphatase can be separated into five fractions that correspond to (I) an anchorless dimer, (II) a tetramer with four glycosylphosphatidylinositol anchor molecules, (III) a tetramer as in (II) with two additional fatty acids bound to inositol on one-half of the tetramer, (IV) an octamer with two fatty acid molecules per alkaline phosphatase subunit and (V) an octamer with three fatty acid molecules per alkaline phosphatase subunit (Bublitz et al., supra). Thus, the number of alkaline phosphatase subunits, the absence or presence of glycosylphosphatidylinositol anchor molecules and the absence or presence of various numbers of fatty acid molecules per subunit contribute to the heterogeneity of the alkaline phosphatase population typically used to prepare labeled oligonucleotide probes. The hydrophobic character of the glycosylphosphatidylinositol anchor molecules and the fatty acid residues in fractions (II) through (V) are believed to contribute to the background noise in nucleic acid hybridization assays.

Unwanted background noise may result from the use of alkaline phosphatase-oligonucleotide conjugate prepared under conditions where conjugates are formed at various sites on the enzyme, including at the enzyme active site. This source of heterogeneity in the enzyme-probe conjugate population results in a label probe with less than ideal specific enzyme activity.

The lack of a homogeneous population of detectably labeled oligonucleotide probes having high specific activity of detection may limit the sensitivity and the precision of typical nucleic acid hybridization assays. Thus, there is a need in the art for improved nucleic acid hybridization assay formats and methods of producing a homogeneous population of detectably labeled oligonucleotide probes having high specific activity of detection and low potential for nonspecific binding.

SUMMARY OF THE INVENTION

Methods are provided for detecting nucleic acid analytes in a sample. In general, the methods involve a solution phase hybridization assays in a competitive, indirect assay format that enables the regulation of hybridization conditions thereby enhancing assay sensitivity and specificity.

It is one object of the invention to provide an indirect, competitive nucleic acid hybridization in which "capture extender" molecules are used, that bind to "label extender" molecules. In a preferred format, capture extenders are bridging probes that bind to support-bound "capture probes" as well as to label extenders and a target nucleotide sequence in an analyte, and label extenders molecules are bridging probes that bind to the capture extenders as well as to "label probes," i.e., oligonucleotide segments having a detectable label bound thereto. In an alternate format, label extenders are bridging probes which bind to label probes as well as to capture extenders and a target nucleotide sequence in an analyte and capture extender molecules are bridging probes that bind to the label extender molecules as well as to capture probes.

It is a second object of the invention to provide a homogeneous population of label probes and methods for their preparation. In one embodiment of the invention, such label probes are incorporated into the novel assay format disclosed and claimed herein. Such label probes have enhanced specific enzyme activity and generate enhanced assay signal detection. The method for preparing such label probes involves purification of anchorless, hydrophilic alkaline phosphatase, conjugation of the enzyme to an oligonucleotide probe under conditions in which the enzyme active site is protected from conjugation and the conjugation of the oligonucleotide to the enzyme is site-directed, and further purification of the label probe thus prepared.

It is an additional object of the invention to provide assay formats having enhanced analyte detection sensitivity and selectivity that incorporate the single molecular form label probes.

In one embodiment of the assay format, a sample containing or suspected of containing an analyte having a target nucleotide sequence is first incubated with a support-bound capture probe/capture extender hybrid complex under first hybridizing conditions. The reaction mixture thus produced, containing uncomplexed capture probe/capture extender hybrids and capture probe/capture extender/analyte complexes, is then incubated with label extender and label probe molecules under second hybridizing conditions. Complexes formed between the uncomplexed capture probe/capture extender hybrids and the label extender/label probe hybrids are then detected. The amount of signal detected is inversely proportional to the quantity of analyte present in the sample.

In another embodiment of the assay format, a sample containing or suspected of containing an analyte containing a target nucleotide sequence is incubated with label probe/label extender hybrid complexes under first hybridizing conditions. The reaction mixture thus produced containing uncomplexed label probe/label extender hybrids and label probe/label extender/analyte complexes is then incubated with capture extender and support-bound capture probe molecules under second hybridizing conditions. Complexes formed between the uncomplexed label probe/label extender hybrids and the capture extender/capture probe hybrids are then detected. The amount of signal detected is inversely proportional to the quantity of analyte present in the sample.

In another embodiment, the invention relates to methods for preparing a homogeneous population of high specific activity alkaline phosphatase-oligonucleotide probe conjugates.

In a further embodiment, the invention relates to novel homogeneous label probes having high specific activity of detection. The alkaline phosphataseoligonucleotide conjugates prepared by the novel methods presently disclosed and claimed have a low potential for nonspecific binding due to the use of a hydrophilic fraction of the enzyme. Furthermore, the conjugates so prepared have high specific enzyme activity because the conjugation of the oligonucleotide to the enzyme is conducted under conditions that inhibit conjugation in the enzyme active site and promote conjugation at particular sites on the enzyme.

The invention also relates to methods of detecting a target oligonucleotide in a sample using alkaline phosphatase-oligonucleotide probes prepared by the novel methods.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Definitions and Nomenclature

Figure 1:
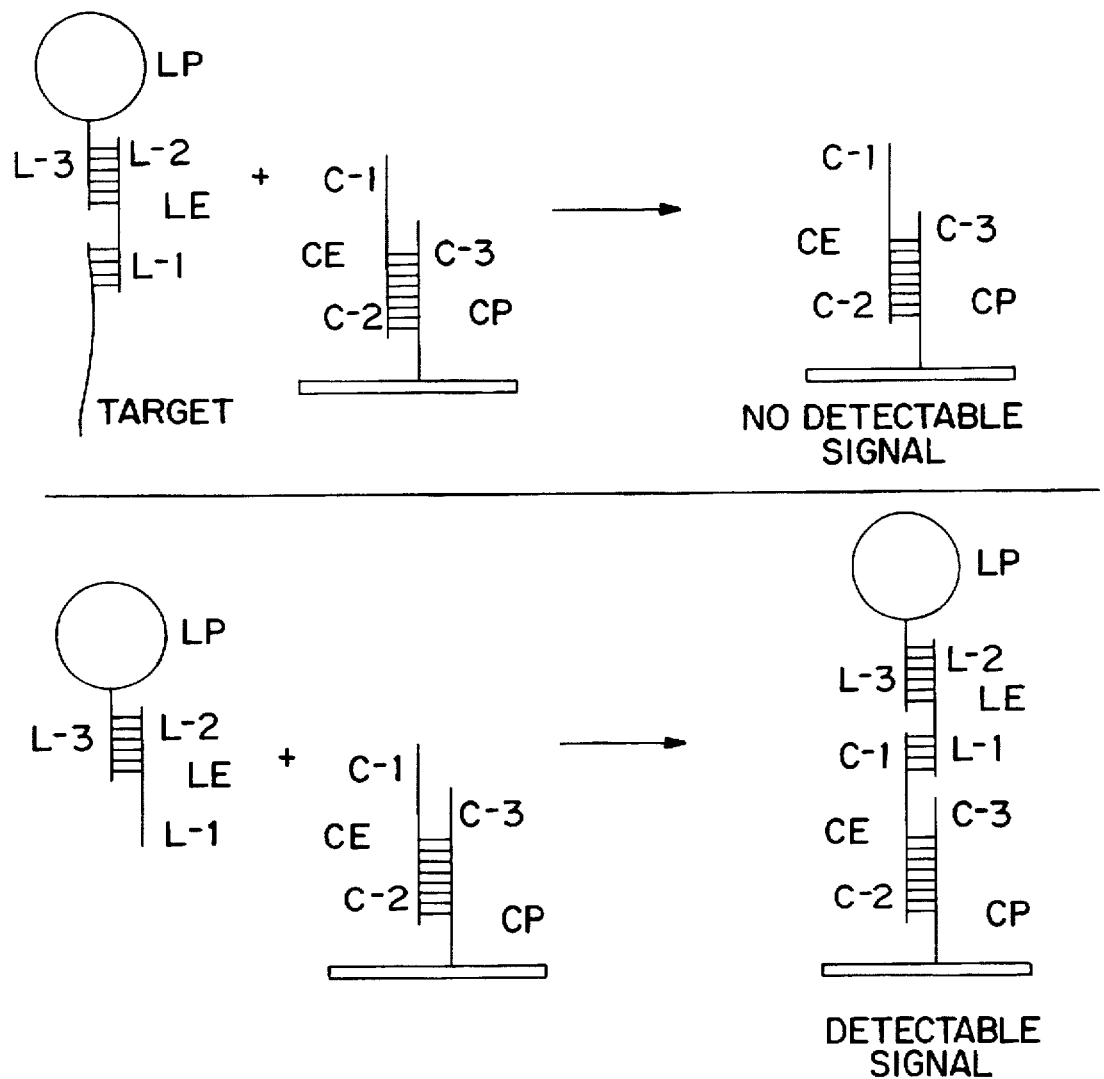
FIG. 1 is a diagram of an indirect, competitive solution phase sandwich hybridization assay format in which a sample is first incubated with a label probe/label extender hybrid complex.

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "a label extender" includes mixtures of such molecules, reference to "a target nucleotide sequence" includes mixtures of two or more such sequences, and the like.

In this specification and in the claims that follow, reference will be made to a number of terms which shall be defined to have the following meanings:

As used herein, the terms "polynucleotide" and "oligonucleotide" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones (e.g., protein nucleic acids and synthetic sequence-specific nucleic acid polymers commercially available from the Anti-Gene Development Group, Corvallis, Oreg., as Neugene™ polymers), providing that the polymers contain nucleobases in a configuration that allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA and DNA:RNA hybrids, and also include known types of modifications, for example, labels that are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties that contain not only the known purine and pyrimidine bases, but also other heterocyclic bases that have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The term "polynucleotide analyte" refers to a single- or double-stranded nucleic acid molecule that contains a target nucleotide sequence. The analyte nucleic acids may be from a variety of sources, e.g., biological fluids or solids, food stuffs, environmental materials, etc., and may be prepared for the hybridization analysis by a variety of means, e.g., proteinase K/sodium dodecyl sulfate ("SDS"), chaotropic salts, or the like. The term "polynucleotide analyte" is used interchangeably herein with the terms "analyte," "analyte nucleic acid," "target" and "target molecule."

As used herein, the term "target region," "target sequence" or "target nucleotide sequence" refers to a probe binding region contained within the target molecule. The term "target sequence" refers to a sequence with which a probe will form a stable hybrid under desired conditions.

As used herein, the term "probe" refers to a structure comprised of a polynucleotide, as defined above, that contains a nucleotide sequence complementary to a nucleotide sequence present in the target molecule. The polynucleotide regions of probes may be composed of DNA, and/or RNA, and/or synthetic nucleotide analogs.

It will be appreciated that the binding sequences need not have perfect complementarity to provide stable hybrids. In many situations, stable hybrids will form where fewer than about 10% of the bases are mismatches, ignoring loops of four or more nucleotides. Accordingly, as used herein, the term "complementary" refers to an oligonucleotide that forms a stable duplex with its "complement" under assay conditions, generally where there is about 90% or greater homology. Typically, such complementary binding sequences will contain approximately 15 to 50, preferably 15 to 30, nucleotides.

The polynucleotides of the invention may be assembled using a combination of solid phase direct oligonucleotide synthesis and enzymatic ligation methods, as described in detail in Ser. No. 07/813,588.

An "alkaline phosphatase active site-protecting agent" refers to a compound which binds to alkaline phosphatase at the active site, thereby protecting amino acids contained in the active site from chemical modification. Such alkaline phosphatase active site-protecting agents may be alkaline phosphatase substrates such as phosphate, substrate analogues such as phosphonic acids and arsonic acid compounds, which are phosphate analogs, or other alkaline phosphatase inhibitors. Preferred alkaline phosphatase active site-protecting agents are competitive inhibitors or other compounds having reversible binding affinity for the active site of the enzyme.

As used herein, a "biological sample" refers to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Preferred uses of the present method are in detecting and/or quantitating polynucleotides encoding viral antigens, such as from hepatitis B virus ("HBV"), hepatitis C virus ("HCV"), hepatitis D virus ("HDV"), human immunodeficiency virus ("HIV"), and the herpes family of viruses, including herpes zoster (chicken pox), herpes simplex virus I & II, cytomegalovirus, Epstein-Barr virus, and the recently isolated Herpes VI virus, and polynucleotides encoding cell products such as cytokines.

As used herein, the term "nonspecific binding" is used to refer to those occurrences in which a polynucleotide binds to the solid support, or other assay component, through an interaction—which may be either direct or indirect—that does not involve hydrogen bonding to support-bound polynucleotides.

By "purified" or "homogeneous" is meant, when referring to a polypeptide or nucleotide sequence, that the indicated molecule is present in the substantial absence of other biological macromolecules of the same type. The term "purified" or "homogeneous" as used herein preferably means at least 90% by weight, more preferably at least 95% by weight, and most preferably at least 98% by weight, of biological macromolecules of the same type present. Thus, a "singular molecular form" of an oligonucleotide, a polypeptide or an oligonucleotide-polypeptide conjugate is a molecule that is present in purified or homogeneous form.

A "uniform population of sites" for an oligonucleotide$_n$— conjugated alkaline phosphatase means that 50%, preferably 75%, more preferably 80%, still more preferably 90%, of the oligonucleotide can be found in n tryptic fragments. For example, a uniform population of sites for an alkaline phosphatase conjugated with a single oligonucleotide is indicated by a single oligonucleotide-containing tryptic fragment of the conjugated alkaline phosphatase.

By "high specific enzyme activity" alkaline phosphatase is meant enzyme activity of at least about 2,000 to 3,000 units per mg enzyme protein. One unit of activity represents the amount of enzyme able to catalyze the conversion of 1 μmol of p-nitrophenyl phosphate to p-nitrophenol per minute in 1M diethanolamine/HCl, pH 9.8.

The term "alcohol" as used herein in refers to primary, secondary or tertiary alcohols, carbinols, and polyhydric alcohols wherein the substituent groups are branched or unbranched, saturated or unsaturated hydrocarbon chains containing 1 to 24 carbon atoms. The term "lower alcohol" intends an alcohol with a substituent group of one to six carbon atoms. Preferred alcohols are primary lower alcohols containing an unbranched saturated hydrocarbon substituent group.

"Optional" or "optionally" means that the subsequently described event or circumstance may or may not occur, and that the description includes instances where said event or circumstance occurs and instances where it does not. For example, the phrase "optionally washed" means that a washing step may or may not occur and that the description of the method includes both proceeding with or without a wash step.

Figure 2:
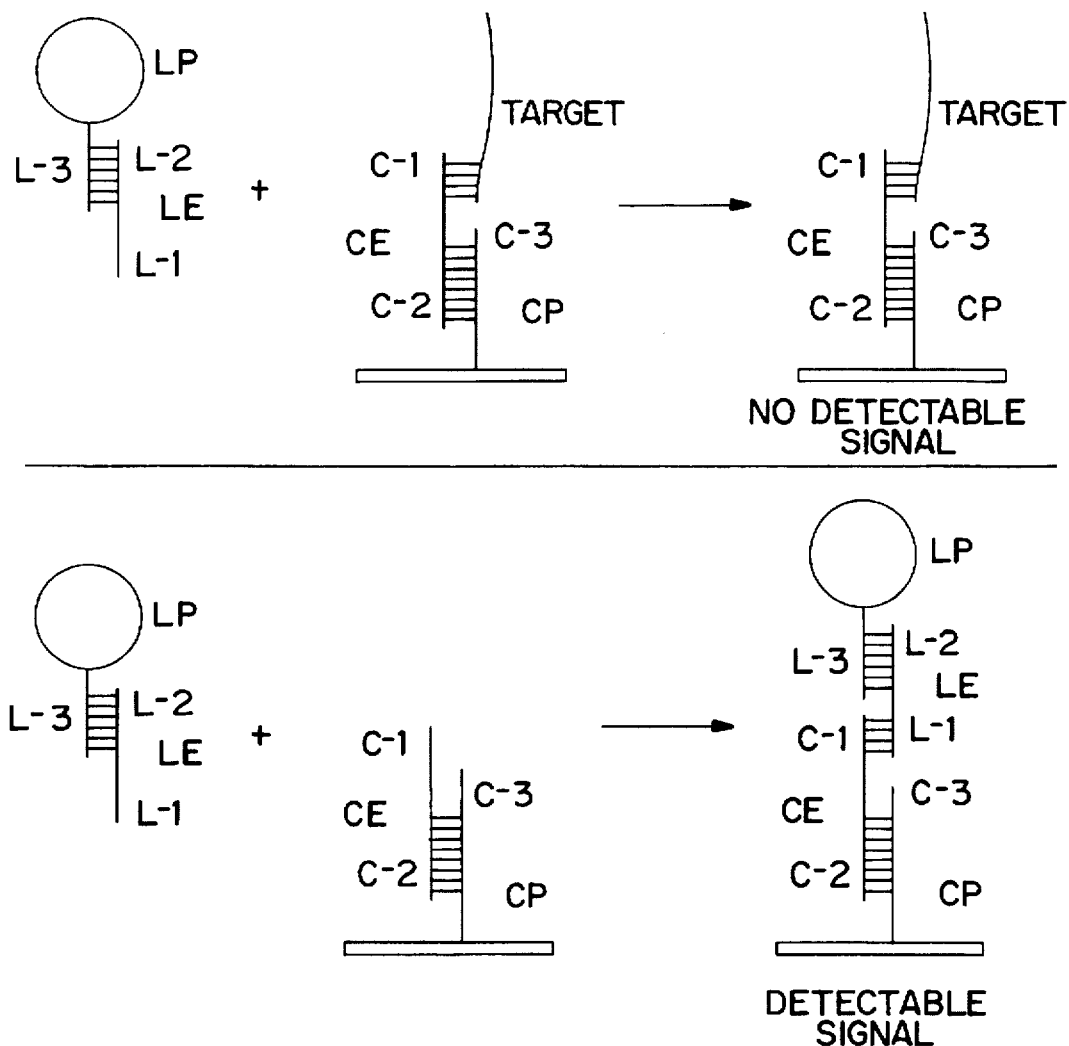
FIG. 2 illustrates an indirect, competitive solution phase sandwich hybridization assay in which a sample is first incubated with a support-bound capture probe/capture extender hybrid complex.

Referring now to the preferred embodiment represented in FIG. 1 and FIG. 2, the following terms apply to the hybridization assay depicted therein.

"Labeled probes (LPs)" are designed to bind to a label extender and contain a label moiety that is capable of generating a detectable signal. Various means for providing labels bound to a nucleic acid sequence have been reported in the literature. See, for example: Leary et al. (1983) Proc. Natl. Acad. Sci. USA 80:4045; Renz et al. (1984) Nucl. Acids Res. 12:3435; Richardson et al. (1983) Nucl. Acids Res. 11:6167; Smith et al. (1985) Nucl. Acids Res. 13:2399; Meinkoth et al. (1984) Anal. Biochem. 138:267; Klibanov et al. (1989) Applied Biochem. Biotechnol. 22:45; Grumbach et al. (1991) J. Immunol. Meth. 140:205; Forgac et al. (1992) Chemicke Listy 86:253; Sehgal et al. (1994) Anal. Biochem. 218:87; and Lewis et al. (1994) Bioconjugate Chem. 5:565. The labels may be bound either covalently or non-covalently (e.g., ionically, or through a high-affinity complex such as a biotin-avidin linkage) to the complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, α-β-galactosidase, horseradish peroxidase, alkaline phosphatase, etc.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels that have been employed in immunoassays and the techniques applicable to immunoassays can be employed with the subject assays.

One preferred label moiety is alkaline phosphatase. Methods of using an alkaline phosphatase substrate with alkaline phosphatase as a label moiety are known in the art (Schaap et al., Tet. Lett. 28:1159–1162 (1987) and EPA Pub. No. 0254051). A preferred substrate for alkaline phosphatase is an enzyme-triggered dioxetane phosphate, more preferred is dioxetane phosphate in the presence of cationic enhancer, such as LumiPhos Plus® (Lumigen), most preferred is a dioxetane in the presence of a cationic enhancer and a hydrophobic monoanionic enhancer. Examples of such hydrophobic monoanionic enhancers are SDS and p-toluene sulfonic acid.

LPs comprise a region having a nucleic acid sequence L-3 complementary to a nucleic acid sequence L-2 present within a label extender and are bound to, or structured so as to bind to, a label that provides, directly or indirectly, a detectable signal. The L-3 sequence is designed to be complementary only to L-2, and vice versa, and not to sequence in any other component of the assay system. The LP may have additional non-complementary regions such as spacer regions flanking sequence L-3.

"Label probe extender molecules (LEs)," also referred to herein as "label extender molecules" or "label extenders," contain regions of complementarity with respect to the analyte polynucleotide and/or, depending on the assay format, the capture extender (L-1) and label probe (L-2). Thus, label extender molecules are single-stranded polynucleotide chains comprising a first region having a nucleic acid sequence L-1 complementary to a sequence of the analyte polynucleotide and/or a sequence of the capture extender, and a second region having a label probe recognition sequence L-2 complementary to a segment L-3 of the label probe. The LE may have additional non-complementary regions such as a spacer region between L-1 and L-2.

Depending on the assay format, "capture probe extender molecules (CEs)," also referred to herein as "capture extender molecules" or "capture extenders," bind to the analyte polynucleotide and/or to the label extender molecule and to capture probes (CPs), that are in turn bound to a solid support. Thus, capture extender molecules are single-stranded polynucleotide chains comprising a first region having a nucleic acid sequence C-1 that is complementary to a sequence of the analyte or to a sequence of the label extender, and a second, noncomplementary region having a capture probe recognition sequence C-2. The CE may have additional non-complementary regions such as a spacer region between C-1 and C-2.

In the assay formats disclosed and claimed herein, either an L-1 or a C-1 nucleic acid sequence that is complementary to a nucleic acid sequence in the analyte, but not both, will be used. In either format, L-1 and C-1 are complementary nucleic acid sequences.

"Capture probes (CPs)" bind to the capture extenders and to a solid support. Thus, as illustrated in FIG. 1, capture probes comprise a first region having a nucleic acid sequence C-3 complementary to C-2 and a second region by which the CPs are covalently bound to (or capable of being covalently bound to) a solid support. The C-3 sequence is designed to be complementary only to C-2, and vice versa, and not to sequence in any other component of the assay system. The CPs may have additional non-complementary regions such as spacer regions flanking sequence C-2. Capture probes may be bound to solid supports as described in PCT Publication No. WO93/13224, the disclosure of which is incorporated by reference herein, to create a solid support for hybridization.

Generally, solution phase hybridization assays carried out using the system illustrated in FIG. 1 proceed as follows. A sample containing or suspected of containing a single-stranded nucleic acid including the target sequence is incubated under first hybridizing conditions with the label probe and label extenders. In this format, the label extender is designed to be capable of forming a bridge between the label probe and the target sequence or the capture extender. The resulting product is a mixture of nucleic acid complexes of the analyte polynucleotide bound to label probe/label extender hybrids and unbound label probe/label extender hybrids. This mixture is then added under second hybridizing conditions to a solid phase having capture extenders hybridized to capture probes bound to the surface thereof. The unbound label probe/label extender hybrid are available to hybridize to the support-bound capture probe/capture extender hybrids.

In this assay format, the presence of the target sequence in the sample depletes the population of label probes that are capable of hybridizing to the support-bound capture probe extender. Thus, the detectable signal that binds to the solid support is quantitatively related to the inverse of the amount of target sequence in the sample.

The quantity of target sequence in the sample, as reflected by the detectable signal generated as described above, may be calculated from a standard curve. A standard curve may be constructed by preparing a standard formulation containing a known quantity of an oligonucleotide comprising a nucleic acid sequence which is identical to the target sequence. A series of dilutions are made using the standard such that the quantity of oligonucleotide in the standard dilution series corresponds to the anticipated range of target sequence quantities in the sample. The standard dilution series can be used in the assay format described above to generate a series of detectable signals that correspond to the known quantities of oligonucleotide in the standard dilution series. The quantity of target sequence in the sample can then be calculated by comparing the signal generated by the sample with the signals generated by the standard dilution series.

An alternative, and preferable, assay format is diagrammed in FIG. 2. In this format, the capture extender is designed to be capable of forming a bridge between the capture probe and the target sequence of the label extender. The sample is initially incubated under first hybridizing conditions with capture extender molecules hybridized to the support-bound capture probe molecules, thereby producing a mixture of support-bound capture probe/capture extender/analyte hybrids and free capture probe/capture extender hybrids. The free capture probe/capture extender hybrids are available to hybridize with subsequently added label probe/label extender hybrid complexes. After addition of the label probe/label extender hybrid complexes the resultant mixture is incubated under second hybridizing conditions to produce detectable capture probe/capture extender/label extender/label probe hybrids and washed to remove unbound label probe/label extender hybrid complexes. The solid phase with bound detectable complexes is then separated from unbound materials, and read.

In this assay format, the presence of the target sequence in the sample depletes the population of support-bound capture extender molecules that are capable of hybridizing to the label probe/label extender hybrids. Thus, as in the format diagrammed in FIG. 1, the detectable signal that binds to the solid support is inversely related to the quantity of target sequence in the sample.

The quantity of target sequence in the sample, as reflected by the detectable signal generated as described above, may be calculated from a standard curve as described above.

Typically, the ratio of the label probe/label extender hybrid or capture probe/capture extender hybrid to anticipated moles of analyte will be greater than about 1:1, preferably at least about 10:1, more preferably at least about 25:1, and possibly as high as 100:1 or higher. Concentrations of each of the probes will generally range from about $10^{-9}$M to $10^{-6}$M, with sample nucleic acid concentrations varying from about $10^{-21}$M to about $10^{-12}$M.

Hybridization steps in the assay formats of the claimed invention are performed under appropriate stringency conditions. Stringency can be controlled by altering a parameter which is a thermodynamic variable. Such variables are well known in the art, and include formamide concentration, salt concentration, chaotropic salt concentration, pH, organic solvent content, and temperature. Preferred stringency controls are pH and salt concentration. The stringency will be varied depending on the length and nature of the target sequence.

The first hybridizing conditions in which a probe-target hybrid is formed are adjusted to provide the desired stringency for the assay. Typically, the first hybridizing conditions are high stringency conditions to increase the specificity of the probe-target hybridization reaction.

The second hybridizing conditions are used when hybrids are formed between sequences that have been designed to hybridize to each other, e.g., to form label probe/label extender or capture probe/capture extender hybrids. Accordingly, the second hybridizing conditions need not be as stringent as the first hybridizing conditions. Preferred second hybridization conditions, approximating physiological conditions, are 37° C., 0.15M monovalent cation, 16 mM $Mg^{++}$, and 1 mM spermidine.

The procedure used in the separation steps of the assay will vary depending upon the nature of the solid phase. For particles, centrifugation or filtration will provide for separation of the particles, discarding the supernatant or isolating the supernatant. Where the particles are assayed, the particles will be washed thoroughly, usually from one to five times, with an appropriate buffered medium, e.g., phosphate buffered saline (PBS) containing a detergent such as SDS. When the separation means is a wall or support, the supernatant may be isolated or discarded and the wall washed in the same manner as indicated for the particles.

An additional focus of the present invention is to enhance both assay specificity by decreasing nonspecific binding, and assay sensitivity, i.e., the ability to distinguish between different nucleic acid sequences. These aims are achieved, in part, by providing a homogeneous population of label probes having high specific activity of label detection.

Preparing such label probes involves, at the outset, providing purified, hydrophilic alkaline phosphatase molecules having high specific enzyme activity. The purified alkaline phosphatase is then conjugated to an oligonucleotide probe containing the L-3 nucleic acid sequence under conditions which control the sites on the enzyme that are available for conjugation. Optionally, the alkaline phosphatase-oligonucleotide conjugate thus formed may be further purified.

A purified hydrophilic alkaline phosphatase preparation may be made using the procedures of Bublitz et al., supra, the disclosure of which is incorporated herein by reference. Bublitz et al. reported that even though a typical alkaline phosphatase preparation may be enzymatically 99% pure, it may consist of more than one fraction of enzyme. Thus, a hydrophilic, anchorless alkaline phosphatase dimer may be prepared from bovine or calf intestinal mucosa or chyme by extracting with a lower alcohol such as butanol, purifying the enzyme by immunoaffinity chromatography and separating the anchorless, hydrophilic dimer fraction from the glycosylphosphatidylinositol-alkaline phosphatase fraction by hydrophobic interaction chromatography, for example, using a phenyl Sepharose® column. Anchorless, hydrophilic alkaline phosphatase dimer can also be prepared from the glycosylphosphatidylinositol-alkaline phosphatase fraction by treatment with phosphatidylinositol-specific phospholipase C or glycosylphosphatidylinositol phospholipase D followed by separation of hydrophilic and hydrophobic fractions by reverse phase chromatography (e.g., octyl Sepharose®).

Alkaline phosphatase may also be obtained and purified from other sources and species including bovine liver, placenta, and kidney, porcine intestinal mucosa, placenta, and kidney, ovine intestinal mucosa, as well as from bacteria such as *Escherichia coli*.

The preparation of label probes with high specific activity of detection involves conjugation of a highly purified oligonucleotide ester to reactive amines on alkaline phosphatase in the presence of a molecule which protects the enzyme active site from conjugation. Thus, during the conjugation reaction, the enzyme active site may be protected by co-incubation with enzyme substrates, for example, phosphates, substrate analogues, or inhibitors, such as phosphonic acids. Techniques for the preparation and purification of oligonucleotide esters are well known in the art. See, for example, Moller et al. (1995) *Bioconjugate Chem.* 6:174 and Ivanovskaya et al. (1994) *Molecular Biol.* 28:754.

Preferably, the alkaline phosphataseoligonucleotide conjugate is made using modifications of the methods described in U.S. Pat. No. 4,868,105 to Urdea et al., supra, and Urdea et al. (1988) *Nucl. Acids Res.* 16:4937–4955, the disclosure of which is incorporated herein by reference.

The method generally involves a first step of reacting the crosslinker with the oligonucleotide to produce an "activated" oligonucleotide. In particular, water-soluble crosslinking agents are preferred, for example, bis (sulfosuccinimidyl)suberate. The ratio of crosslinker to oligonucleotide may be varied independently to optimize the reaction-product. In general, the crosslinker may be present in excess sufficient to avoid the formation of crosslinked oligonucleotide dimers. Accordingly, the crosslinker:oligonucleotide ratio will be in the range of about 5 to 100, preferably about 5 to 25, and most preferably 5 to 10.

The preparation of a homogeneous population of label probes involves the next step of conjugating the alkaline phosphatase to the activated oligonucleotide under conditions wherein the reactivity of the amines on the enzyme can be modulated to direct the conjugation to a uniform population of reactive sites in the enzyme. Due to the microenvironments of amine groups in alkaline phosphatase, the reactivity of the amines may be controlled by varying the pH of the conjugation reaction conditions, thereby directing the conjugation to a uniform population of reactive sites. In addition, the ratio of the activated oligonucleotide to alkaline phosphatase may be varied between 5 and 100 or higher. This yields a label probe in which an oligonucleotide is conjugated to a uniform population of amines.

The pH of the conjugation reaction may be varied to yield an enzyme-oligonucleotide conjugate having desired (e.g., maximum) enzyme activity by altering the buffer composition of the reaction solution. For example, in order to buffer the conjugation reaction in the appropriate range of physiological pH, i.e., in the range of about pH 6.6 to pH 8.0, more typically in the range of about pH 7.2 to pH 7.8, a phosphate buffer may be used. Phosphate, as an alkaline phosphatase substrate, provides protection of the enzyme active site. Alternative buffering compositions capable of providing a reaction mixture at a desired pH are well known in the art and may be found in, for example, the CRC Handbook of Chemistry and Physics, D. R. Lide, ed., 1994. Differential reactivity of protein amine groups as a function of pH in reactions using crosslinking agents has been reported by Grumbach et al., supra. The differential pH dependence of hydrolysis and aminolysis reactions of crosslinking agents with proteins has been described by Anjaneyulu et al. (1987) Int. J. Peptide Protein Res. 30:117–124.

The ratio of oligonucleotide to alkaline phosphatase in the label probe (i.e., the number of conjugated sites on the enzyme) may be determined by analytical gel electrophoresis using techniques well known in the art. In addition, the population of alkaline phosphatase sites conjugated to oligonucleotides can be determined digesting the oligonucleotide-conjugated enzyme and performing amino acid analysis on the digest using techniques well known in the art. Enzyme activity of the label probe may be determined and compared to the enzyme activity of the purified alkaline phosphatase. High specific activity label probes, preferably having 75% to 100%, more preferably 80% to 100%, and most preferably 90% to 100% of the enzyme activity of the starting materials are then used in nucleic acid hybridization assays.

Optionally, the label probe may be further purified using ion exchange chromatography, hydrophobic interaction chromatography (e.g., phenyl Sepharose®), reverse phase chromatography (e.g., octyl Sepharose®), chromatofocusing, or the like. Alternatively, and in general preferably, the label probe is further purified using affinity chromatography as described, for example, in Landt et al. (1978) Biochem. 17:915–919, the disclosure of which is incorporated herein by reference. Affinity chromatography using alkaline phosphatase substrates or substrate analogues has the added benefit of providing label probes which have intact alkaline phosphatase binding sites.

This procedure may be used to provide high specific-activity label probes for use in virtually any type of hybridization assay wherein label probe molecules are used, including a wide range of solution phase hybridization assays, amplification assays, filter hybridization methods, assays involving the polymerase chain reaction ("PCR"), and the like. One example of a hybridization assay with which the present technique is useful is that described in U.S. Pat. No. 4,868,105 to Urdea et al., or, preferably, that described above in conjunction with the configuration illustrated in FIG. 1 and FIG. 2 and described above.

The invention provides novel assays that are specific (e.g., able to recognize single nucleotide differences between analyte nucleic acid sequences), sensitive (e.g., able to quantitate attomole amounts of analyte nucleic acids) and easily automated. Thus, the invention is particularly useful in blood screening assays and genotype or subtype assays. The invention is particularly suitable for mutational analysis of genomic DNA or RNA and other structural analyses of nucleic acids. In addition, the invention may be used to monitor gene therapy or anti-sense drugs and for mapping discontinuous probes that bind tightly to nucleic acid targets for use in diagnostics or as antisense therapeutics as described in commonly assigned U.S. application Ser. No. 08/349,316 to Collins, filed Dec. 5, 1994, entitled "Discontinuous Probe Design Using Hybritope Mapping."

Experimental

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, Molecular Cloning: A Laboratory Manual, Second Edition (1989); Oligonucleotide Synthesis (M. J. Gait, ed., 1984); Nucleic Acid Hybridization (B. D. Hames & S. J. Higgins, eds., 1984); and a series, Methods in Enzymology (Academic Press, Inc.). All patents, patent applications, and publications mentioned herein, both supra and infra, are hereby incorporated by reference.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

An oligonucleotide marked with a superscript "c" denotes an oligonucleotide which is complementary to the oligonucleotide not so marked. Thus, "target$^c$" is an oligonucleotide which contains a target sequence which is complementary to "target." An oligonucleotide marked with a superscript "$^c$" denotes an oligonucleotide which is complementary to an oligonucleotide marked with a superscript "c." Thus, "target$^{cc}$" denotes an oligonucleotide which contains a nucleic acid sequence which is complementary to "target$^c$."

EXAMPLE 1

Preparation of Labelled Probe

Oligonucleotide probes were prepared using an anchorless, hydrophobic preparation of alkaline phosphatase. The process of conjugating the oligonucleotide probe was conducted under conditions which selectively direct the conjugation to a uniform population of sites on the enzyme and in the presence of phosphate to insure that the active site on the enzyme will not be available for conjugation. A homogeneous population of alkaline phosphatase-oligonucleotide conjugates was produced after further purification of the conjugate using additional chromatography steps.

A. Purification of Alkaline Phosphatase. Alkaline phosphatase was purified from a commercially available source to produce an anchorless, hydrophilic preparation as follows.

Alkaline phosphatase (Boehringer Mannheim) was concentrated, and the buffer in which the enzyme was originally supplied was exchanged for 10 mM Tris HCl, pH 8.0, in a Centricon-30 (Amicon) concentrator that had been rinsed with 10 mM Tris HCl, pH 8.0. The enzyme and 10 mM Tris HCl, pH 8.0, were added and the concentrator was centrifuged at 3000–4000×g. This process was repeated twice.

An alkaline phosphatase affinity column was prepared according to the method of Landt et al., supra. The column was poured using approximately 1 ml of L-histidyldiazobenzylphosphonic acid resin suspension (Sigma) per mg of alkaline phosphatase. The poured column was packed by running 10 mM Tris HCl, pH 8.0, through at a rate of about 10–20 ml/hr. The optical density of the column effluent was monitored at 280 nm until the $OD_{280}$ was approximately 0.00.

The washed, concentrated alkaline phosphatase was applied to the packed column at a rate of 10–20 ml/hr. The column was washed using 10 mM Tris HCl to remove impurities which do not specifically bind to the resin. The retained alkaline phosphatase was eluted by 10 mM $Na_2HPO_4$ in 10 mM Tris HCl, pH 8.0.

Collected fractions containing alkaline phosphatase was concentrated using a Centriprep-30 (Amicon) or Centricon-30, or both, as described above. The concentrated alkaline phosphatase was washed into 100 mM phosphate buffer, pH 7.2, at 4° C. or alkaline phosphatase storage buffer containing 3M sodium chloride, 1 mM magnesium chloride, 0.1 mM zinc chloride, 30 mM triethylamine, pH 7.4.

B. Conjugation of alkaline phosphatase to an oligonucleotide probe to form the label probe. The 3'-long chain amine ("LCA") portion (X) of the bla3 oligonucleotide (5'-AAGTACGACAACCACATCX-3')(SEQ ID No: 1), wherein X is is $N^4$-(6-aminocaproyl-2-aminoethyl)-cytosine, is activated using bis(sulfosuccinimidyl)suberate ("$BS^3$") (Pierce) in a 1:10 ratio of bla3:$BS^3$. Thus, $BS^3$ (21.5 mg) and bla3 (274 nmoles/ml) are added to 100 mM phosphate buffer, pH 7.8, and incubated for 30 min at room temperature.

The reaction mixture is applied to a NAP-5 column (Pharmacia) previously equilibrated with 100 mM phosphate buffer, pH 6.5, at 4° C. The desired product is eluted using 100 mM phosphate buffer, pH 6.5, at 4° C. If desired, the activated oligonucleotide may be further purified using an ethanol precipitation step.

In order to provide a label probe according to the method of the invention, the conjugation reaction can be conducted at various pHs and DNA:enzyme ratios to determine the desired conjugation conditions. The activated, purified bla3 is added to approximately 100 nmoles/ml of the affinity-purified alkaline phosphatase in 100 mM phosphate buffer, pH 7.2, or pH 7.8, at 4° C., at a DNA:enzyme ratio of 5:1, 25:1 or 100:1, and incubated for 30 min at 4° C. The reaction product is concentrated and washed into alkaline phosphatase storage buffer using a Centricon-30. The washing step is repeated three times to insure that unreacted DNA flows through the filter membrane and is minimized in the product.

If necessary, the alkaline phosphatase oligonucleotide conjugate may be further purified using, for example, ion exchange chromatography, hydrophobic chromatography, reverse phase chromatography, chromatofocusing or affinity chromatography. The ratio of label to DNA is determined using analytical gel electrophoresis. Enzymatic activity is determined using conventional assay techniques (see Landt et al., supra). The labeled reactive amines are determined by digesting the conjugated alkaline phosphatase and performing amino acid analysis using conventional techniques.

EXAMPLE 2

Detection of HIV Rev Response Element Probe #8730

This assay was done using the assay format diagrammed in FIG. 2 to detect the presence of a human immunodeficiency virus Rev response element probe ("the RRE probe") having the sequence 5'-TCCTGCTGCTCCCAAGAA-3' (SEQ ID No: 2). Extracts of MOLT-3 cells (ATCC CRL 1552), cytoplasmic or nuclear, were separated by centrifugation and spiked with various amount of the RRE probe to simulate quantitation of therapeutic antisense molecules in cells.

50 µl of amp diluent (50% horse serum, 0.05% sodium azide, 1.3% SDS, 5X SSC (20X SSC contains 175 gm/l sodium chloride and 88 g/l sodium citrate), 0.5 mg/ml proteinase K, 6 mM Tris-HCl, 0.05% Proclin 300® (Rohm-Haas) and 0.006 mM phenylmethylsulfonyl fluoride) containing 1 fmol/well of the capture extender "$PSCP^c$-target$^{c'}$" (5'-TTCTTGGGAGCAGCAGGACTCTTGGAAAGAA AGTGAAGTG-3')(SEQ ID No: 3) was added to microtiter wells to which the capture probe "PSCP" (5'-XCACTTCACTTTCTTTCCAAGAG-3')(SEQ ID No: 4), wherein X is as defined above, was bound. After 30 min at 37° C., the wells were washed 2-times with wash buffer A (0.1% SDS, 0.1X SSC, 0.05% sodium azide and 0.05% Proclin 300®). For the data shown in Tables 1 and 2, 50 µl of cellular extracts corresponding to 0, 24,000, 48,000 or 72,000 MOLT-3 cells containing 0, 2, 4, 6 or 8 fmol of the RRE probe was added to the wells. For the data shown in Table 2, 50 µl of cellular extracts corresponding to 0, 60,000, 120,000 or 180,000MOLT-3 cells containing 0, 2, 4, 6 or 8 fmol of the RRE probe was added to the wells. The reaction mixture was incubated for 30 min at 37° C. The wells were washed two times with wash buffer A.

The alkaline phosphatase-bla3 label probe prepared according to the method described in Example 1 was added to amp diluent containing label extender bla3$^c$-target$^{c'}$ (5'-GATGTGGTTGTCGTACTTTCCTGCTGCTCCCAAG AA-3')(SEQ ID No: 5) in a final volume of 100 µl. The reaction mix was incubated for 30 min at 37° C. The reaction mix was diluted with label diluent and added to the wells at a final concentration of 5 fmol per 50 µl.

After incubating the reaction mix for 1 hr at 37° C., the microtiter wells were washed twice with wash buffer A and then twice with wash buffer D (0.1% Brij-35, 5 mM magnesium chloride, 0.1M Tris-HCl, 0.01% sodium azide and 0.01% Proclin 300®). 50 µl dioxetane with LumiPhos Plus® (Lumigen) and 0.03% SDS was added to the washed microtiter wells. The microtiter plates were incubated for 30 min at 37° C. and the signal generated was detected.

The data tabulated in Tables 1 and 2 indicate that the assay is linear over the range of the probe concentration tested, that the precision (as reflected by the %C.V.) is very high, and that the presence of a nuclear extract of MOLT-3 cells does not interfere with the detection of the probe.

TABLE 1

| Addition of Cytoplasmic Extracts from MOLT-3 Cells | | | | |
|---|---|---|---|---|
| PROBE (fmoles) | Avg. Signal | Standard Deviation | % C.V. | Signal - Noise |
| 0 Cells | | | | |
| 0 | 779.65 | 26.22 | 0.03 | 775.47 |
| 2 | 641.68 | 45.26 | 0.07 | 637.50 |
| 4 | 496.43 | 15.73 | 0.03 | 492.25 |
| 6 | 361.13 | 12.53 | 0.03 | 356.95 |
| 8 | 317.53 | 11.12 | 0.04 | 313.35 |
| 24,000 Cells | | | | |
| 0 | 823.48 | 10.10 | 0.01 | 818.99 |
| 2 | 680.75 | 47.93 | 0.07 | 676.26 |
| 4 | 480.45 | 18.41 | 0.04 | 475.96 |
| 6 | 369.28 | 16.43 | 0.04 | 364.79 |
| 8 | 279.28 | 17.08 | 0.06 | 274.79 |
| 48,000 Cells | | | | |
| 0 | 824.13 | 10.93 | 0.01 | 819.74 |
| 2 | 678.98 | 69.74 | 0.10 | 674.59 |
| 4 | 485.32 | 20.68 | 0.04 | 480.94 |
| 6 | 384.33 | 5.76 | 0.01 | 379.94 |
| 8 | 280.63 | 6.07 | 0.02 | 276.24 |

TABLE 1-continued

Addition of Cytoplasmic Extracts from MOLT-3 Cells

| PROBE (fmoles) | Avg. Signal | Standard Deviation | % C.V. | Signal - Noise |
|---|---|---|---|---|
| 72,000 Cells | | | | |
| 0 | 787.48 | 24.82 | 0.03 | 782.08 |
| 2 | 666.93 | 64.31 | 0.10 | 661.53 |
| 4 | 481.65 | 29.15 | 0.06 | 476.25 |
| 6 | 389.28 | 10.63 | 0.03 | 383.88 |
| 8 | 292.98 | 13.27 | 0.05 | 287.58 |

TABLE 2

| PROBE (fmoles) | NUCLEAR EXTRACT ADDED (NUMBER OF CELLS) | | | |
|---|---|---|---|---|
| | 0 | 60,000 | 120,000 | 180,000 |
| 0 | 788.4 | 771.6 | 815.4 | 777.6 |
| 2 | 625.0 | 614.9 | 644.5 | 664.7 |
| 4 | 436.5 | 468.4 | 456.2 | 455.9 |
| 6 | 335.4 | 352.1 | 357.7 | 347.0 |
| 8 | 266.1 | 263.8 | 269.1 | 307.9 |

We claim:

1. A label probe comprising a purified hydrophilic alkaline phosphatase conjugated to an oligonucleotide probe.

2. The label probe of claim 1, wherein the purified hydrophilic alkaline phosphatase consists essentially of alkaline phosphatase dimer.

3. The label probe of claim 1, wherein the oligonucleotide is conjugated to a uniform population of sites on the alkaline phosphatase.

4. A method of detecting a target oligonucleotide in a sample, comprising:

a) providing a support-bound capture probe (CP) comprising a region having a nucleic acid sequence C-3;

b) providing a label probe (LP) comprising a region having a nucleic acid sequence L-3, wherein the label probe contains a label moiety that is capable of generating a detectable signal;

c) providing a label extender (LE) comprising a region having first and second nucleic acid sequences, wherein the first LE nucleic acid sequences L-2 is complementary to nucleic acid sequences L-3 and the second LE nucleic acid sequence L-1 is complementary to a nucleic acid sequence in the target analyte;

d) providing a capture extender (CE) comprising a region having first and second nucleic acid sequences, wherein the first CE nucleic acid sequences C-2 is complementary to nucleic acid sequence C-3 and the second CE nucleic acid sequence C-1 is complementary to the second LE nucleic acid sequence L-1;

e) incubating the sample with the LE and the LP under first hybridizing conditions to form a first reaction mixture containing an LP/LE/target hybrid complex and an unbound LP/LE hybrid complex;

f) incubating the first reaction mixture with a solid support surface containing a surface-bound CE/CP hybrid complex under second hybridizing conditions, thereby forming a second reaction mixture containing a surface-bound LP/LE/target/CE/CP hybrid complex and an unbound LP/LE/target complex;

g) thereafter separating materials not bound to the solid support from those bound to the solid support;

h) detecting the presence of label in the support-bound, LP/LE/target/CE/CP hybrid complex; and (i) correlating the presence of the label with the presence of the target oligonucleotide in the sample.

5. The method of claim 4, wherein the label moiety is selected from the group consisting of fluorescein, rhodamine, Texas red, phycoerythrin, umbelliferone, luminol, NADPH, α-β-galactosidase, horse-radish peroxidase and alkaline phosphatase.

6. The method of claim 5, wherein the label moiety is alkaline phosphatase.

7. The method of claim 6, wherein the label probe is prepared according to the method comprising:

(a) providing a purified hydrophilic alkaline phosphatase; and (b) conjugating the hydrophilic alkaline phosphatase with an oligonucleotide probe.

8. The method of claim 6, wherein the label probe is prepared according to the method comprising:

(a) providing a purified hydrophilic alkaline phosphatase;

(b) conjugating the hydrophilic alkaline phosphatase with an oligonucleotide probe under reaction conditions in which the oligonucleotide probe is conjugated to a uniform population of sites on the alkaline phosphatase.

9. The method of claim 8, wherein in step (b) the alkaline phosphatase is conjugated to the oligonucleotide probe in the presence of an alkaline phosphatase active site-protecting agent.

10. The method of claim 7, wherein the purified hydrophilic alkaline phosphatase consists essentially of alkaline phosphatase dimer.

11. The method of claim 6, wherein the label probe is prepared according to the method comprising:

(a) providing an alkaline phosphatase;

(b) conjugating the alkaline phosphatase with an oligonucleotide probe under reaction conditions in which the oligonucleotide probe is conjugated to a uniform population of sites on the alkaline phosphatase.

12. The method of claim 11, wherein in step (b) the alkaline phosphatase is conjugated to the oligonucleotide probe in the presence of an alkaline phosphatase active site-protecting agent.

13. A method of detecting a target oligonucleotide in a sample, comprising:

a) providing a support-bound capture probe (CP) comprising a region having a nucleic acid sequence C-3;

b) providing a label probe (LP) comprising a region having a nucleic acid sequence L-3, wherein the label probe contains a label moiety that is capable of generating a detectable signal;

c) providing a capture extender (CE) comprising a region having first and second nucleic acid sequences, wherein the first CE nucleic acid sequences C-2 is complementary to nucleic acid sequence C-3 and the second CE nucleic acid sequence C-1 is complementary to a nucleic acid sequence in the target analyte;

d) providing a label extender (LE) comprising a region having first and second nucleic acid sequences, wherein the first LE nucleic acid sequences L-2 is complementary to nucleic acid sequences L-3 and the second LE nucleic acid sequence L-1 is complementary to the second CE nucleic acid sequence C-1;

e) incubating the sample with the CE and the CP under first hybridizing conditions to form a first reaction mixture containing CP/CE/target hybrid complex and unbound CP/CE hybrid complexes;

f) incubating the first reaction mixture with an LE/LP hybrid complex under second hybridizing conditions, thereby forming a second reaction mixture containing a surface-bound LP/LE/target/CE/CP hybrid complex and an unbound LP/LE complex;

g) thereafter separating materials not bound to the solid support from those bound to the solid support;

h) detecting the presence of label in the support-bound, LP/LE/target/CE/CP hybrid complex; and (i) correlating the presence of the label with the presence of the target oligonucleotide in the sample.

14. The method of claim 13, wherein the label moiety is selected from the group consisting of fluorescein, rhodamine, Texas red, phycoerythrin, umbelliferone, luminol, NADPH, $\alpha$-$\beta$-galactosidase, horse-radish peroxidase and alkaline phosphatase.

15. The method of claim 14, wherein the label moiety is alkaline phosphatase.

16. The method of claim 15, wherein the label probe is prepared according to the method comprising:

(a) providing a purified hydrophilic alkaline phosphatase; and (b) conjugating the hydrophilic alkaline phosphatase with an oligonucleotide probe.

17. The method of claim 15, wherein the label probe is prepared according to the method comprising:

(a) providing a purified hydrophilic alkaline phosphatase;

(b) conjugating the hydrophilic alkaline phosphatase with an oligonucleotide probe under reaction conditions in which the oligonucleotide probe is conjugated to a uniform population of sites on the alkaline phosphatase.

18. The method of claim 17, wherein in step (b) the alkaline phosphatase is conjugated to the oligonucleotide probe in the presence of an alkaline phosphatase active site-protecting agent.

19. The method of claim 15, wherein the purified hydrophilic alkaline phosphatase consists essentially of alkaline phosphatase dimer.

20. The method of claim 15, wherein the label probe is prepared according to the method comprising:

(a) providing an alkaline phosphatase;

(b) conjugating the alkaline phosphatase with an oligonucleotide probe under reaction conditions in which the oligonucleotide probe is conjugated to a uniform population of sites on the alkaline phosphatase.

21. The method of claim 20, wherein in step (b) the alkaline phosphatase is conjugated to the oligonucleotide probe in the presence of an alkaline phosphatase active site-protecting agent.

22. The method of claim 7, wherein in step (b) the alkaline phosphatase is conjugated to the oligonucleotide probe in the presence of an alkaline phosphatase active site-protecting agent.

23. The method of claim 16, wherein in step (b) the alkaline phosphatase is conjugated to the oligonucleotide probe in the presence of an alkaline phosphatase active site-protecting agent.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 19
        ( D ) OTHER INFORMATION: /standard_name= "N4-(6-aminocaproyl-2-aminoethyl)cytosine"

( x i ) SEQUENCE DESCRIPTION: SEQ ID NO:1:

AAGTACGACA ACCACATCN                                               19

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCCTGCTGCT CCCAAGAA                                                 18

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

-continued ( x i ) SEQUENCE DESCRIPTION: SEQ ID NO:3:

TTCTTGGGAG CAGCAGGACT CTTGGAAAGA AAGTGAAGTG                40

( 2 ) INFORMATION FOR SEQ ID NO:4:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: misc_feature
      ( B ) LOCATION: 1
      ( D ) OTHER INFORMATION: /standard_name=
         " N4-(6-aminocaproyl-2-aminoethyl)cytosine"

( x i ) SEQUENCE DESCRIPTION: SEQ ID NO:4:

NCACTTCACT TTCTTTCCAA GAG                23

( 2 ) INFORMATION FOR SEQ ID NO:5:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

GATGTGGTTG TCGTACTTTC CTGCTGCTCC CAAGAA                36